United States Patent
Von Berg et al.

(10) Patent No.: US 11,058,383 B2
(45) Date of Patent: Jul. 13, 2021

(54) APPARATUS FOR THE DETECTION OF OPACITIES IN X-RAY IMAGES

(71) Applicant: KONINKLIJKE PHILIPS N.V., Eindhoven (NL)

(72) Inventors: Jens Von Berg, Hamburg (DE); Stewart Young, Hamburg (DE); Daniel Bystrov, Hamburg (DE); Nataly Wieberneit, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 64 days.

(21) Appl. No.: 16/347,825

(22) PCT Filed: Oct. 26, 2017

(86) PCT No.: PCT/EP2017/077376
§ 371 (c)(1),
(2) Date: May 7, 2019

(87) PCT Pub. No.: WO2018/086893
PCT Pub. Date: May 17, 2018

(65) Prior Publication Data
US 2019/0254618 A1 Aug. 22, 2019

(30) Foreign Application Priority Data
Nov. 8, 2016 (EP) .................... 16197665

(51) Int. Cl.
*A61B 6/00* (2006.01)
*G16H 30/40* (2018.01)
*G06T 7/00* (2017.01)

(52) U.S. Cl.
CPC .............. *A61B 6/5205* (2013.01); *A61B 6/48* (2013.01); *G06T 7/0014* (2013.01); *G16H 30/40* (2018.01);
(Continued)

(58) Field of Classification Search
CPC ......... A61B 6/5205; A61B 6/48; A61B 6/463; G16H 30/40; G06T 2207/10116;
(Continued)

(56) References Cited

U.S. PATENT DOCUMENTS

| | | |
|---|---|---|
| 2003/0112921 A1 | 6/2003 | Lang |
| 2004/0175034 A1 | 9/2004 | Wiemker |

(Continued)

FOREIGN PATENT DOCUMENTS

| | | |
|---|---|---|
| WO | WO2011077334 A1 | 6/2011 |
| WO | WO2011135484 A1 | 11/2011 |
| WO | WO2015157067 A1 | 10/2015 |

OTHER PUBLICATIONS

Schilham Arnold M.R. et al., "A Computer-Aided Diagnosis System for Detection of Lung Nodules in Chest Radiographs with an Evaluation on a Public Database", Medical Image Analysis, 10, 2006, pp. 247-258.

(Continued)

*Primary Examiner* — Christopher M Brandt
(74) *Attorney, Agent, or Firm* — Larry Liberchuk (57) ABSTRACT

The present invention relates to an apparatus for the detection of opacities in X-ray images. It is described to provide (210) an analysis X-ray image of a region of interest of an analyzed body part. A model of a normal region of interest is provided (220), wherein the model is based on a plurality of X-ray images of the region of interest. At least one abnormality is detected (230) in the region of interest of the analyzed body part, the detection comprising comparing the analysis X-ray image of the region of interest and the model of the normal region of interest. Information is output (240) on the at least one abnormality.

13 Claims, 4 Drawing Sheets

(52) U.S. Cl.
CPC ..... *A61B 6/463* (2013.01); *G06T 2207/10116* (2013.01); *G06T 2207/20128* (2013.01); *G06T 2207/30061* (2013.01)

(58) Field of Classification Search
CPC . G06T 2207/20128; G06T 2207/30061; G06T 7/0014
See application file for complete search history.

(56) References Cited

U.S. PATENT DOCUMENTS

| | | | |
|---|---|---|---|
| 2007/0122078 A1 | 5/2007 | Huo | |
| 2008/0037853 A1 | 2/2008 | Bernard | |
| 2009/0052763 A1 | 2/2009 | Acharyya | |
| 2009/0238432 A1* | 9/2009 | Can | G06T 7/001 382/132 |
| 2010/0111386 A1 | 5/2010 | El-Baz | |
| 2011/0188719 A1* | 8/2011 | Ishii | A61B 6/501 382/128 |
| 2013/0044927 A1* | 2/2013 | Poole | G06T 7/0014 382/131 |

OTHER PUBLICATIONS

Van Ginneken B. et al., "Automated Scoring of Chest Radiographs for Tuberculosis Prevalence Surveys: A Combined Approach", Proc. Fifth International Workshop on Pulmonary Image Analysis, pp. 9-19, 2013.

Jaeger S. et al., "Detecting Tuberculosis in Radiographs Using Combined Lung Masks", Engineering in Medicine and Biology Society (EMBC), 2012 34th Annual International Conference of the IEEE. EMBS, pp. 4987-4981, Sep. 1, 2012.

Barthel D. et al., "Robust Automatic Lung Field Segmentation on Digital Chest Radiographs", Int J CARS, 4(Suppl 1):326-327, 2009.

Von Berg J. et al., "A Novel Bone Suppression Method That Improves Lung Nodule Detection", International Journal of Computer Assisted Radiology and Surgery, pp. 1-15, 2015.

Von Berg J. et al., "Decomposing the Bony Thorax in RX-Ray Images", In Proc of 2016 IEEE 13th International Symposium on Biomedical Imaging (ISBI), Apr. 2016, 10.1109/ISBI.2016.7493450.

Rueckert D. et al., "Nonrigid Registration Using Free-Form Deformations: Application to Breast MR Images", IEEE Transactions on Medical Imaging, vol. 18, No. 8, Aug. 1999, pp. 712-721.

Jaeger S. et al., "Automatic Tuberculosis Screening Using Chest Radiographs", IEEE Transactions on Medical Imaging, vol. 33, No. 2, Feb. 2014, pp. 233-245.

Ahemd B. et al., "Rib Suppression for Enhancing Frontal Chest Radiographs Using Independent Component Analysis", International Conference on Adaptive and Natural Computing Algorithms, ICANNGA 2007: Adaptive and Natural Computing Algorithms pp. 300-308, 2007.

Requena-Mendez A. et al., Robust and reproducible Quantification of teh Extenrt of Chest Radioggraphic Abnormalities (and it's free!), PLOS ONE, 10(5), May 21, 2015.

Oda, Seitaro et al "Performance of Radiologists in Detection of Small Pulmonary Nodules on Chest Radiographs: Effect of Rib Suppression with a Massive-Training Artificial Neural Network", American Journal of Roentgenology, vol. 193, No. 5, Nov. 1, 2009, pp. W397-W402.

* cited by examiner

APPARATUS FOR THE DETECTION OF OPACITIES IN X-RAY IMAGES

FIELD OF THE INVENTION

The present invention relates to an apparatus for the detection of opacities in X-ray images, to a system for the detection of opacities in X-ray images, and to a method for the detection of opacities in X-ray images, as well as to a computer program element and a computer readable medium.

BACKGROUND OF THE INVENTION

Contrary to other diseases, treatment of tuberculosis (TB) by antibiotics is (in many cases) cheap and very effective. However, despite the existence of such potentially successful therapeutic strategies, TB remains a severe health problem in many parts of the world. The primary reason for this is the lack of access to healthcare, and the associated delays in identification and diagnosis of patients within the time-window when successful treatment is feasible.

US2013/044927A1 describes a method of detecting the presence of an abnormality in image data. The method comprises acquiring an image data set representative of an image of a subject, acquiring a statistical atlas representative of normal image data sets obtained from a plurality of reference subjects, comparing the image data to the statistical atlas, and determining the presence of an abnormality by determining a measure of the difference between the image data and the statistical atlas.

Chest radiography plays a crucial role in rapid case identification, providing a potential method for quickly screening individuals at risk or with suspicious symptoms, and furthermore to obtain a relatively detailed characterization of the nature of any suspected active TB findings. Again, some of the key issues in the effective deployment of potentially decisive technologies in the fight against TB relate to access to healthcare resources in many developing countries. With regard to chest X-rays this issue often manifests itself not only in the access to the imaging hardware itself, but also in the availability of trained staff to perform the imaging exams, and especially to perform the reading of chest radiographs. Image interpretation is frequently carried out by staff with insufficient expertise, who could benefit from inexpensive and easy to use support, e.g. via a software tool automatically analysing these images.

Therefore, algorithms to support medical staff in the task of detecting and characterising TB in chest radiographs are highly desirable, due to a shortage of well-trained personnel in large parts of the world. In developed parts of the world such algorithms would also free up the time of clinicians, aid in their training, and aid in the diagnostic process. Existing methods use quite complex image features such as shape and texture descriptors to detect TB.

The above requirement to aid in the assessment of radiographs in relation to TB also applies to other pulmonary diseases, and to the assessment of mammograms. There is also a need to improve the assessment of X-ray imagery used in for example non-destructive testing, and imagery used for security purposes, for example scanning luggage at airports.

SUMMARY OF THE INVENTION

It would be advantageous to have an improved technique for interpreting X-ray imagery.

The object of the present invention is solved with the subject matter of the independent claims, wherein further embodiments are incorporated in the dependent claims. It should be noted that the following described aspects of the invention apply also for the apparatus for the detection of opacities in X-ray images, the system for the detection of opacities in X-ray images, the method for the detection of opacities in X-ray images, and for the computer program element and the computer readable medium.

According to a first aspect, there is provided an apparatus for the detection of opacities in clinical X-ray images, comprising:

an input unit;
a processing unit; and
an output unit.

The input unit is configured to provide the processing unit with an analysis X-ray image of a region of interest of an analyzed body part. The input unit is also configured to provide the processing unit with a model of a normal region of interest, wherein the model is based on a plurality of X-ray images of the region of interest that is normal and does not suffer from abnormalities, and wherein the model contains statistical information on a normal healthy population. The processing unit is configured to detect at least one abnormality in the region of interest of the analyzed body part. The detection comprises a comparison between the analysis X-ray image of the region of interest and the model of the normal region of interest. The detection also comprises suppression of at least some bone related imagery in the analysis X-ray image. The output unit is configured to output information on the at least one abnormality.

In other words, X-ray images of a region of interest (for example a lung) that is normal, and does not suffer from abnormalities, is used to build a model of a normal region of interest. This model can be based on data from a wide selection of the healthy population, and forms a normal model with statistical information on such a normal healthy population. Such statistical information can be captured within a Gaussian modelling framework, a Poisson modelling framework, or any other suitable modelling framework for example. A principal component model of the whole lung field is another modelling option that would account for global properties of the lung. An abnormality in for example a lung of a patient can then be determined through a comparison between an X-ray image of that person's lung and the model.

In this way, abnormalities in the region of interest can be automatically detected, and no sophisticated training or machine learning algorithms are required. Thus, utility of provision is provided to cross-sections of the community who frequently do not have access to techniques for the detection of diseases such as tuberculosis. Being able to reliably indicate if there is an abnormality in the region of interest also means that a reliable indication can be provided that there is no abnormality, which also has utility because a reliable indication can be made that a patient does not need to be referred for further investigative analysis.

The apparatus provides an indication of abnormality that is physiologically plausible and intuitive, because detection of abnormalities is based on a comparison of an X-ray image with a model generated from normal X-ray images that do not show abnormalities. In this way, a clinician can choose a selection of X-ray images for a population that exhibit no abnormalities, from which a normal model can be built. Then this model can be used to determine if a patient has an abnormality in for example a lung through a comparison of an X-ray of their lung and the normal model. Accurate, and simple, prediction of abnormalities is provided.

In an example, the comparison between the analysis X-ray image of the region of interest and the model of the normal region of interest comprises the processing unit being configured to determine at least one deviation between at least one intensity in the region of interest of the analysis X-ray image and a corresponding at least one intensity in the normal region of interest of the model.

Thus, intensities at positions within a model generated on the basis of a number of normal X-ray images exhibits statistical information on the normal intensities expected across an image. The deviation in intensities between an acquired image can the intensities in the model that carry statistical information regarding a normal region of interest, such as a lung, can be used to determine if there is one or more abnormalities (or not) in the lung of a patient on the basis of the acquired image of their lung. Thus, a reliable indication can be made that a patient has an abnormality and similarly a reliable indication can be made that the patient has no abnormalities in the body part (such as a lung).

In this manner, a straightforward and easily interpreted means is provided for determining abnormalities because it is based on the intensities in images and the deviation in intensities between an acquired X-ray and that that would be expected for a statistically normal person (the modelled). Thus, the apparatus is mimicking what a skilled clinician would like to be able to do, in terms of comparing an X-ray with a representation of what it should look like in order to determine if abnormalities exist.

In an example, model data comprises at least one average intensity based on corresponding intensities in the plurality of X-ray images of the region of interest and the model data comprises at least one standard deviation intensity based on the corresponding intensities in the plurality of X-ray images of the region of interest. The comparison between the analysis X-ray image of the region of interest and the model of the normal region of interest is based on at least one intensity value in the region of interest of the analysis X-ray image and on the at least one average intensity value in the normal region of interest of the model and on the at least one standard deviation intensity in the normal region of interest of the model.

In this manner, by considering an average intensity in the model and a standard deviation a statistically significant determination can be made on whether features in the acquired X-ray image constitute abnormalities or not.

Such a normal model, comprising mean and standard deviation values, has a relatively small number of parameters and is conceptually very simple to apply and interpretation of results from the model is intuitive and physiologically plausible.

In an example, the comparison between the analysis X-ray image of the region of interest and the model of the normal region of interest comprises the processing unit being configured to determine a difference between an intensity at a spatial position in the analysis X-ray image of the region of interest and an average intensity at a corresponding spatial position in the model of the normal region of interest and comprises the processing unit being configured to determine a ratio between this difference and a standard deviation in intensity at the corresponding spatial position in the model of the normal region of interest.

In this way, parts of X-ray images, relating to particular parts of a region of interest such as the root of the pulmonary vessel tree (hilus), that have strong opacities and therefore associated high image intensities will lead to a model having a relatively high intensity level and relatively high standard deviation at that region. Providing a ratio between the difference between the mean model intensity and analyzed intensity at that region and the standard deviation in intensity at the corresponding spatial position, means that in effect a normalised score value is provided. This determines a measure of deviation from the norm at that position, but also provides a means of comparing a score with other parts of the image. For example, in this way areas of abnormality can be delineated.

Also, areas of X-ray images that have associated large variations in intensity levels even for a healthy population, will when compared with the analyzed intensity at that position be normalised by a relatively large standard deviation, resulting in a reduction in false positive indications of abnormalities.

In an example, the detection of at least one abnormality in the region of interest of the analyzed body part comprises the processing unit being configured to determine at least one score based on at least one intensity in the region of interest of the analysis X-ray image and a corresponding at least one intensity in the normal region of interest of the model.

In this way, a score can be used to indicate if there is an abnormality and to identify where abnormalities exist, and even to delineate the determined extent of an abnormality.

In an example, a score is used to indicate that at least one abnormality has been detected in the region of interest of the analyzed body part.

In this manner, a simple yes/no indication can be provided that the analyzed image relates to a person who has an abnormality in a region of a body part. The person can then be referred for further diagnostic work-up, and/or the analyzed image can be reviewed by a clinician to determine the next course of action.

In other words, the at least one abnormality can be marked.

In an example, the processing unit is configured to delineate at least one area of the region of interest of the analysis X-ray image on the basis of the at least one score.

In other words, a score can be used to provide information on a statistically significant deviation from normality, for example where a score of zero relates to a normal intensity level at a position in an analyzed image and a score of 2 relates to an intensity level that is two standard deviations away from what is expected. Regions having a score above a certain level, 0.2. 0.3. 0.4, . . . 1.0, 1.2, 1.3 . . . 1.9, 2.0, 2.1 . . . 2.6, 2.7, . . . etc can then be identified. Not only does this identify where an abnormality is, but identifies its extent, and also enables statistical artefacts such as isolated ones, twos, threes of pixels that have a high score to be determined to be related to statistical fluctuations, and not evidence of an abnormality. In this way, an outline of the abnormality can be indicated.

In an example, detection of the at least one abnormality in the region of interest of the analyzed body part comprises the processing unit being configured to suppress at least some bone related imagery in the analysis X-ray image.

In other words, bones which overlay a region of interest, such as a lung field, can impose opacities that are stronger than those associated with the abnormalities that are sought to be detected. The regions of bone are identified, and opacities that are determined relating to those bones are in effect subtracted from the acquired imagery, to result in an image that would have been expected to have been acquired if the bones were not present. This helps facilitate abnormality detection.

In an example, the plurality of X-ray images of the region of interest, upon which the model of the normal region is based, have had at least some bone related imagery suppressed.

In an example, detection of the at least one abnormality in the region of interest of the analyzed body part comprises the processing unit being configured to intensity normalize the analysis X-ray image.

In this manner, exposure intensity and duration and size of the patient can be taken into account.

In an example, the plurality of X-ray images of the region of interest, upon which the model of the normal region is based, have been intensity normalized. In an example, detection of the at least one abnormality in the region of interest of the analyzed body part comprises a registration of the region of interest of the analysis X-ray image to the normal region of interest of the model.

In other words, the image being analyzed is spatially normalized with the model, such that locations in the region of interest (e.g. in the lung field) are aligned with anatomically corresponding locations in the model.

According to a second aspect, there is provided a system for the detection of opacities in X-ray images, the system comprising:

at least one image acquisition unit; and an apparatus for the detection of opacities in clinical X-ray images according to the first aspect.

The at least one image acquisition unit is configured to provide the analysis X-ray image. The output unit is configured to output the analysis X-ray image comprising the information on the at least one abnormality.

According to a third aspect, there is provided an automated method for the detection of opacities in X-ray images, comprising:

a) providing an analysis X-ray image of a region of interest of an analyzed body part;

b) providing a model of a normal region of interest, wherein the model is based on a plurality of X-ray images of the region of interest that is normal and does not suffer from abnormalities, and wherein the model contains statistical information on a normal healthy population;

c) detecting at least one abnormality in the region of interest of the analyzed body part, the detection comprising comparing the analysis X-ray image of the region of interest and the model of the normal region of interest and suppressing at least some bone related imagery in the analysis X-ray image; and d) outputting information on the at least one abnormality.

According to another aspect, there is provided a computer program element controlling apparatus as previously described which, when the computer program element is executed by a processing unit, is adapted to perform the method steps as previously described.

According to another aspect, there is provided a computer readable medium having stored computer element as previously described.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
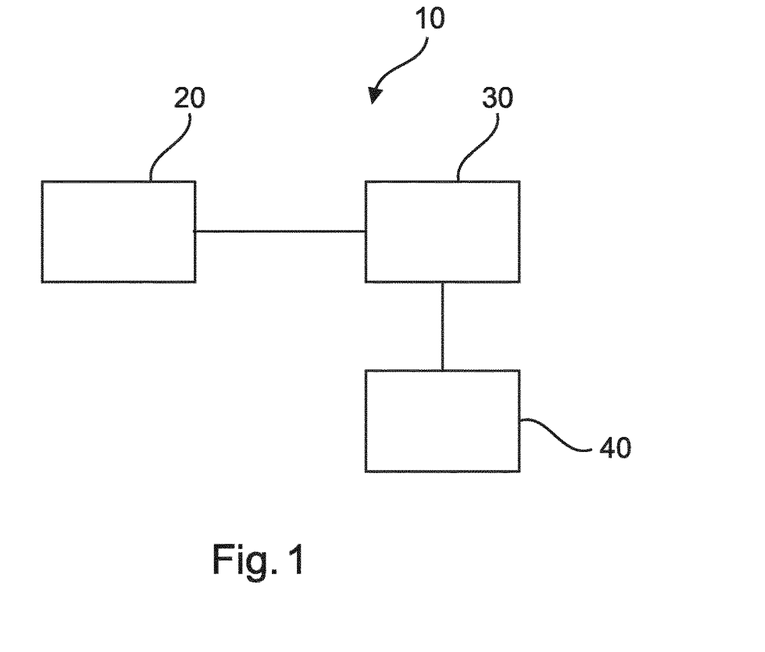
FIG. 1 shows a schematic set up of example of an apparatus for the detection of opacities in X-ray images.

FIG. 1 shows an example of an apparatus 10 for the detection of opacities in X-ray images. The apparatus 10 comprises an input unit 20, a processing unit 30, and an output unit 40. The input unit 20 is configured to provide the processing unit 30 with an analysis X-ray image of a region of interest of an analyzed body part, via wired or wireless communication. The input unit 20 is also configured to provide the processing unit 30 with a model of a normal region of interest, via wired or wireless communication. The model is based on a plurality of X-ray images of the region of interest. The processing unit 30 is configured to detect at least one abnormality in the region of interest of the analyzed body part. The detection comprises a comparison between the analysis X-ray image of the region of interest and the model of the normal region of interest. The output unit 40 is configured to output information on the at least one abnormality.

In an example, the analysis image is a radiograph, or attenuation X-ray image. In an example, the analysis image is a dark field image. In an example, the analysis image is a phase contrast image. In an example, the plurality of images comprises radiographs, or attenuation X-ray images. In an example, the plurality of images comprises dark field images. In an example, the plurality of images comprises phase contrast images.

In an example, the region of interest relates to a lung.

In an example, the at least one abnormality relates to one or more pulmonary diseases. In an example, the at least one abnormality relates to tuberculosis. In other words, a pulmonary disease such as tuberculosis could have resulted in the at least one abnormality.

According to an example, the comparison between the analysis X-ray image of the region of interest and the model of the normal region of interest comprises the processing unit being configured to determine at least one deviation between at least one intensity in the region of interest of the analysis X-ray image and a corresponding at least one intensity in the normal region of interest of the model.

According to an example, model data comprises at least one average intensity based on corresponding intensities in the plurality of X-ray images of the region of interest. The model data also comprises at least one standard deviation in intensity, based on the corresponding intensities in the plurality of X-ray images of the region of interest. The comparison between the analysis X-ray image of the region of interest and the model of the normal region of interest is then based on at least one intensity value in the region of interest of the analysis X-ray image and on the at least one average intensity value in the normal region of interest of the model and on the at least one standard deviation intensity in the normal region of interest of the model.

According to an example, the comparison between the analysis X-ray image of the region of interest and the model of the normal region of interest comprises the processing unit being configured to determine a difference between an intensity at a spatial position in the analysis X-ray image of the region of interest and an average intensity at a corresponding spatial position in the model of the normal region of interest. The comparison also comprises the processing unit being configured to determine a ratio between this difference and a standard deviation in intensity at the corresponding spatial position in the model of the normal region of interest.

According to an example, the detection of at least one abnormality in the region of interest of the analyzed body part comprises the processing unit being configured to determine at least one score based on at least one intensity in the region of interest of the analysis X-ray image and a corresponding at least one intensity in the normal region of interest of the model.

According to an example, a score is used to indicate that at least one abnormality has been detected in the region of interest of the analyzed body part.

In an example, the indication comprises utilisation of a colour to mark an abnormality. In an example, the specific colour being used can be linked to the score. In this way, a simple colour coding can be used to help indicate a severity of the abnormality. For example, for a score that is only just above a threshold value a yellow colour could be used to indicate the abnormality, whilst for a score that is significantly greater than the threshold a bright red colour could be used to mark the abnormality. In this manner, not only is a simple means provided to indicate that there is abnormality and indicate its location, a simple means is provided to indicate the possible severity of the abnormality. In this way, an unskilled person in the field is able to prioritise cases that have been indicated as having abnormalities.

According to an example, the processing unit is configured to delineate at least one area of the region of interest of the analysis X-ray image on the basis of the at least one score.

According to an example, detection of the at least one abnormality in the region of interest of the analyzed body part comprises the processing unit being configured to a suppress at least some bone related imagery in the analysis X-ray image.

According to an example, the plurality of X-ray images of the region of interest, upon which the model of the normal region is based, have had at least some bone related imagery suppressed.

According to an example, detection of the at least one abnormality in the region of interest of the analyzed body part comprises the processing unit being configured to intensity normalize the analysis X-ray image.

According to an example, the plurality of X-ray images of the region of interest, upon which the model of the normal region is based, have been intensity normalized. According to an example, detection of the at least one abnormality in the region of interest of the analyzed body part comprises a registration of the region of interest of the analysis X-ray image to the normal region of interest of the model.

In an example, the plurality of X-ray images of the region of interest, upon which the model of the normal region is based, have been registered to one another.

Figure 2:
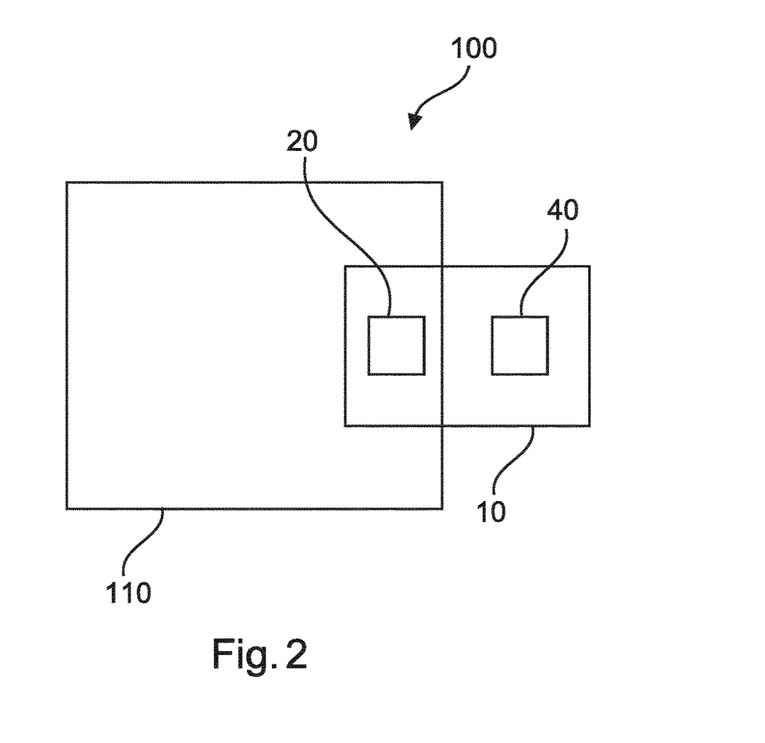
FIG. 2 shows a schematic set up of an example of a system for the detection of opacities in X-ray images.

FIG. 2 shows an example of a system 100 for the detection of opacities in X-ray images. The system 100 comprises at least one image acquisition unit 110, and an apparatus 10 for the detection of opacities in X-ray images as described in relation to FIG. 1. The at least one image acquisition unit 110 is configured to provide the analysis X-ray image, via wired or wireless communication. The providing can be to the input unit 20. The output unit 40 is configured to output the analysis X-ray image comprising the information on the at least one abnormality.

In an example, the input unit 20 is an image acquisition unit of the at least one acquisition unit 110.

In an example, the at least one image acquisition unit is configured to acquire the plurality of X-ray images of the region of interest.

In an example, the at least one image acquisition unit comprises a grating based differential phase contrast and dark field X-ray imaging device. In an example, the at least one image acquisition unit comprises an interferometer arrangement.

In an example, the at least one image acquisition unit comprises an X-ray imaging device. For example, the device can be a tomography arrangement, or a CT arrangement.

In an example, the at least one image acquisition unit is a standard radiography device, with transmitted intensities of radiation providing information on attenuation through the object.

In an example, the at least one image acquisition unit can operate in a Differential phase contrast imaging (DPCI) mode.

In an example, the at least one image acquisition unit generates an attenuation image, relating to the detection of intensity (intensity) values of X-rays with and without the object in the examination region.

In an example, the at least one image acquisition unit generates a phase contrast (or differential phase) image, relating to the detection of the phases of the X-rays with and without the object in the examination region. In an example, the at least one image acquisition unit generates a dark field (or de-coherence) image, relating to the detection of fringe visibilities of the X-rays with and without the object in the examination region.

In an example, the output unit outputs an absorption (or attenuation) image. In an example, the output unit outputs a phase contrast (or differential phase) image. In an example, the output unit outputs a dark field image.

In an example, the output unit outputs data on a monitor such as a visual display unit or on a number of separate monitors. For example, attenuation, phase contrast and dark field images can be presented on a monitor.

In an example, the system has useful application in a clinical environment such as a hospital. In an example, the system can be used for the detection of pulmonary diseases, in mammography, diagnostic radiology and interventional radiology for the medical examination of patients.

In an example, the system has useful application in an industrial environment, for example in non-destructive testing (e.g. analysis as to composition, structure and/or qualities of biological as well non-biological samples) as well as security scanning (e.g. scanning of luggage in airports).

Figure 3:
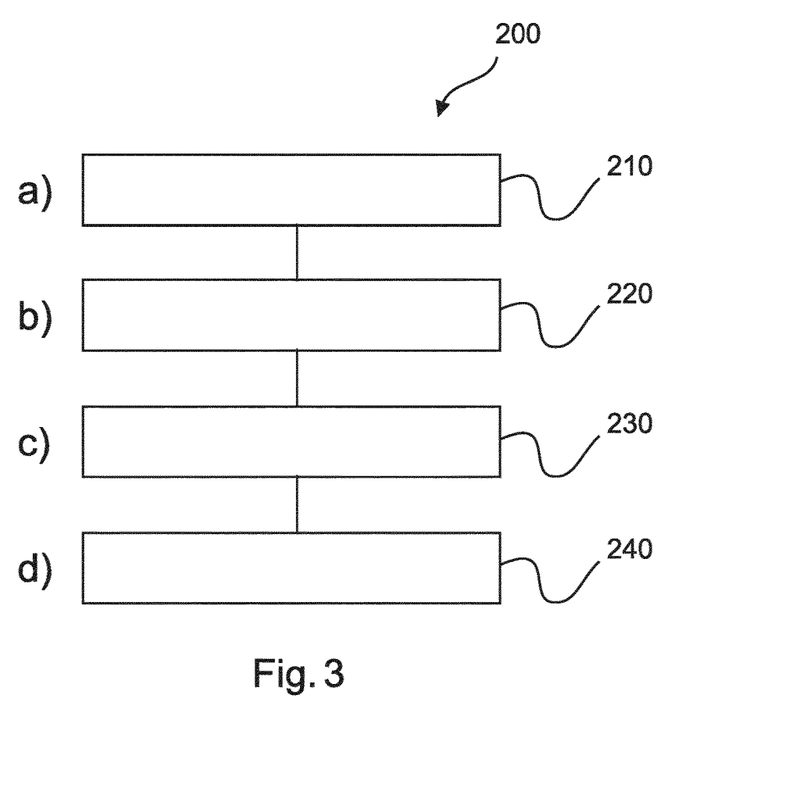
FIG. 3 shows an example of a method for the detection of opacities in X-ray images.

FIG. 3 shows a method 200 for the detection of opacities in X-ray images in its basic steps. The method comprises:

in a providing step 210, also referred to as step a), providing an analysis X-ray image of a region of interest of an analyzed body part;

in a providing step 220, also referred to as step b), providing a model of a normal region of interest, wherein the model is based on a plurality of X-ray images of the region of interest;

in a detecting step 230, also referred to as step c), detecting at least one abnormality in the region of interest of the analyzed body part, the detection comprising comparing the analysis X-ray image of the region of interest and the model of the normal region of interest; and in an outputting step 240, also referred to as d), outputting information on the at least one abnormality.

In step a), the providing can be from an input unit 20 to a processing unit 30.

In step b), the providing can be from the input unit to the processing unit.

In step c), the detecting can be performed by the processing unit.

In step d), the outputting can be performed by an output unit.

In an example, step c) comprises determining of at least one deviation between at least one intensity in the region of interest of the analysis X-ray image and a corresponding at least one intensity in the normal region of interest of the model.

In an example, the model provided in step b) comprises model data comprising at least one average intensity based on the corresponding intensities in the plurality of X-ray images of the region of interest and the model data comprises at least one standard deviation intensity based on the corresponding intensities in the plurality of X-ray images of the region of interest. In step c) the comparison between the analysis X-ray image of the region of interest and the model of the normal region of interest can then be based on at least one intensity value in the region of interest of the analysis X-ray image and on the at least one average intensity value in the normal region of interest of the model and on the at least one standard deviation intensity in the normal region of interest of the model.

In an example, step c) comprises determining a difference between an intensity at a spatial position in the analysis X-ray image of the region of interest and an average intensity at a corresponding spatial position in the model of the normal region of interest and comprises determining a ratio between this difference and a standard deviation in intensity at the corresponding spatial position in the model of the normal region of interest.

In an example, step c) comprises determining at least one score based on at least one intensity in the region of interest of the analysis X-ray image and a corresponding at least one intensity in the normal region of interest of the model.

In an example, a score is used to indicate that at least one abnormality has been detected in the region of interest of the analyzed body part.

In an example, step c) comprises delineating at least one area of the region of interest of the analysis X-ray image on the basis of the at least one score.

In an example, step c) comprises suppressing at least some bone related imagery in the analysis X-ray image.

In an example, step c) comprises normalizing of at least one intensity of the analysis X-ray image.

In an example, step c) registering the region of interest of the analysis X-ray image to the normal region of interest of the model.

Examples of the apparatus, system and method for the detection of opacities in X-ray images will now be described in more detail in conjunction with FIGS. 4-7.

Several existing alternative approaches for the automated detection of tuberculosis lesions in chest radiographs have been proposed, based upon automated measurement of different image features, including texture features (see the paper by van Ginneken, Bram, et al. "Automated Scoring of Chest Radiographs for Tuberculosis Prevalence Surveys: A Combined Approach." Proc. Fifth International Workshop on Pulmonary Image Analysis. 2013), and shape features of opacities. The shape of the lung fields has also been proposed as a basis for TB detection (see the paper by van Ginneken et al and the paper by Jaeger, Stefan, et al. "Detecting tuberculosis in radiographs using combined lung masks." Engineering in Medicine and Biology Society (EMBC), 2012 Annual International Conference of the IEEE. IEEE, 2012), whereby opacities adjacent to the pleura yield an indirect indicator for the presence of parenchymal lesions. However, the results of computer aided decision systems based on a variety of technical features are hard to verify by the user. Intuitive indicators of the analysis results are crucial in order to establish the confidence of the user in the results, and this is therefore a significant limitation of such approaches. Furthermore, the training of these algorithms typically requires a large number of annotated images. Also, the specifically trained algorithms turn out to be very sensitive to external parameters like noise, several kinds of image artefacts, and image post-processing parameters. Therefore, it is not straightforward to apply the trained algorithm to images from different sets of images obtained under deviating conditions to the training set, as is required in real world situations.

The apparatus, system and method for the detection of opacities in X-ray images described here addresses these issues, as discussed above in relation to FIGS. 1-3 and as discussed in more detail below.

The radiological manifestation of TB in the lung is caused by localised accumulation of fluids or fibrous tissue at locations where lung parenchyma was present prior to infection. This change in the physiological properties of the lung tissues causes localised opacity (due to an increased absorption of X-rays) to be present in the chest x-ray image. Automated detection of opacities in areas of the radiograph corresponding to the lung fields, as provided by the apparatus here described, is a very direct and physiologically plausible approach to detect tuberculosis in chest radiographs automatically.

To achieve this, a number of complications have to be taken into account, in order that such opacities relating to abnormalities can be identified. Complications that are addressed by the apparatus, system and method for the detection of opacities in X-ray images include:

i. Bones overlaid with the lung field also impose opacities stronger than those induced by tuberculosis;

ii. According to different acquisition protocols (exposure) and patient properties (weight/size) image intensities in the lung field may vary significantly stronger than by variations induced by tuberculosis and therefore counteracts quantitative comparison between images; and iii. The root of the pulmonary vessel tree (hilus) imposes strong opacities.

Similar issue arise in the detection of other pulmonary diseases, and in the analysis of mammograms for example.

Figure 4:
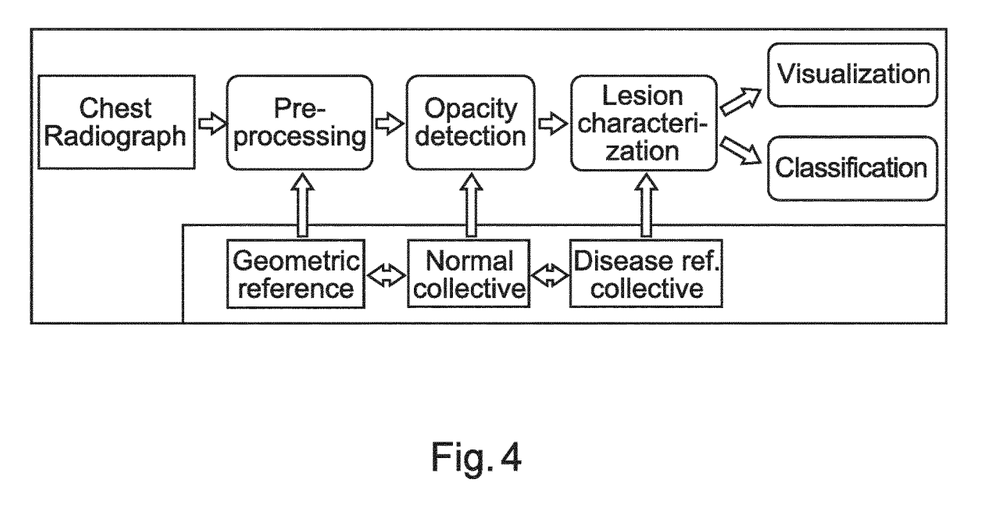
FIG. 4 shows an example of a detailed workflow for the detection of opacities in X-ray images.

FIG. 4 shows an example of a detailed workflow for the detection of opacities in X-ray images as provided by the apparatus, system and method for the detection of opacities in X-ray images described here. An approach is provided for the automated detection and characterization of opacities in X-ray images, such as chest radiographs. The four main elements of the approach can be summarized, for the case of chest radiographs, as:
1. Pre-processing of a chest radiograph;
2. Comparison of a chest radiograph with a Normal Model;
3. Detection of abnormalities in a chest radiograph; and
4. Classification of detected abnormalities from chest radiograph In essence, the approach enables a direct comparison of chest radiographs to one another, and thereby a method to enable comparing an "unseen" image with a multitude of "known" images. The selection of the images can be performed by an expert, and thereby evaluated according to some pre-defined set of inclusion criteria, and the information derived from this image "database" forms the basis of a comparison analysis to detect deviations from the expectations encoded in this database.

Specific steps of the detailed workflow shown in FIG. 4 are now described in more detail.

Pre-Processing

In order to account for the complications (i and ii) outlined above, pre-processing is performed for each image: The following pre-processing steps are applied:
1. Segmentation of the lung fields;
2. Bone suppression;
3. Intensity normalization of the lung fields; and
4. Spatial normalization of the lung fields.

Figure 5:
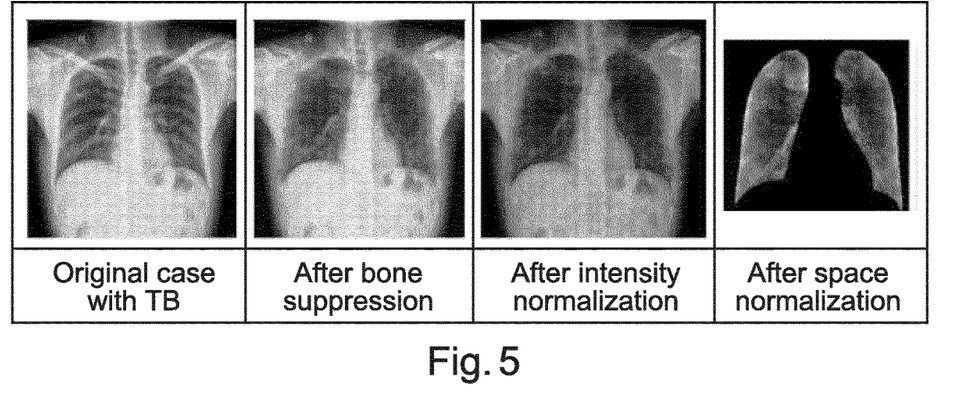
FIG. 5 shows images relating to different pre-processing steps in an example of a method for the detection of opacities in X-ray images.
Figure 6:
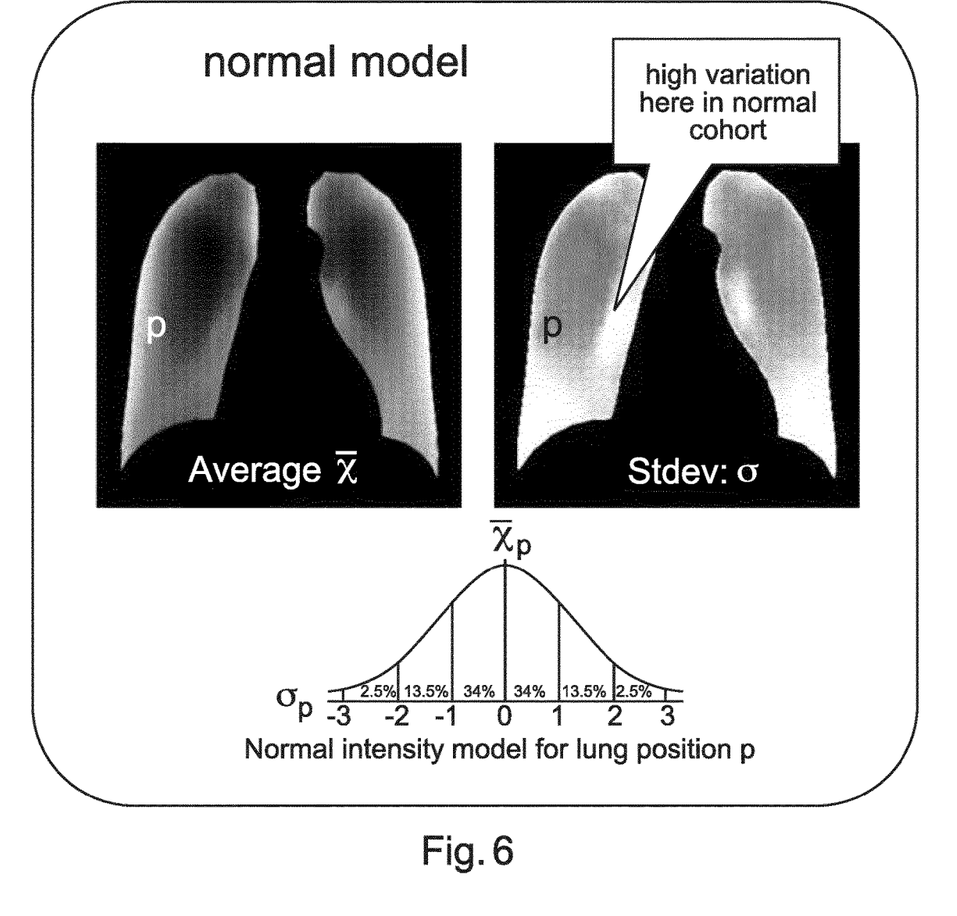
FIG. 6 shows modeling of the distribution of intensities in a lung in an example of a method for the detection of opacities in X-ray images.

FIG. 5 shows results from an example case for the different phases of pre-processing. After these steps the intensities in the lung field can be quantitatively analyzed. Signal outside the lung fields is neglected, rib structures overlaid within the lung fields are suppressed, and the influence of exposure or patient weight is compensated in the intensity normalization step. Spatial normalization (or registration) also aligns anatomically corresponding locations of the lung field.

Normal Model

A statistical model is built from a collection of normal cases (defined as radiologically normal, meaning no significant radiological findings were observed by experts in the images) describing the intensity distribution (average av_i (x) and standard deviation stddev(x)) at any location in the atlas. This model provides a confidence interval of the expected intensity in the atlas space for normals based on average and standard derivation (See FIG. 6, where modeling the distributions of intensities in the lung field for a set of normal subjects in a common atlas space is shown—a Gaussian model is used with average and standard deviation). There are dark areas in the average lung field (central upper part), and there are brighter areas (base, lateral band, hilus). The standard derivation of the expected intensity also varies spatially across the atlas space. For example, variation is larger in the hilus and in the base of the lungs, but not at the lateral band. This normal model, comprising mean and standard deviation, has a comparatively low number of parameters and is conceptually very simple to apply. Only a small number of data sets are required for training, and there is a low risk of over-fitting towards a particular selection of training cases.

Abnormality Detection

An image, acquired for example from a subject in the field and can be considered to be an analysis X-ray image, is analyzed by:
1. Pre-Processing it; and
2. Detecting any abnormal image location.

The deviation from the confidence interval (z score at x) at any position in the lung field is detected:

$$z(\bar{x}) = [I(\bar{x}) - \mu(\bar{x})]/\sigma(\bar{x})$$

where $I(\bar{x})$ is image intensity at location $\underline{x}$, $\mu(\underline{x})$ is average intensity at $\underline{x}$ in the normal model, and $\sigma(x)$ is the standard deviation at $\underline{x}$ in the normal model.

Figure 7:
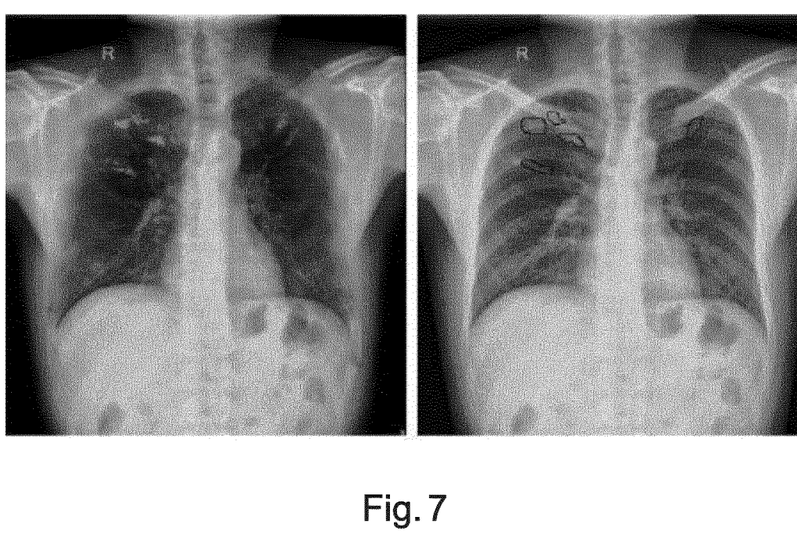
FIG. 7 shows images indicating abnormal image regions resulting as output from an example of an apparatus for the detection of opacities in X-ray images.

The result is illustrated in FIG. 7, where abnormal image regions with a high z-scores are indicated by a solid overlay on the left hand image and as contours delineating an area of abnormality on the right hand image. It can be seen that image intensity alone is not decisive for a region to be marked (or detected). For example, although the hilar areas are bright they are not marked, because the standard deviation in the normal model is also large in this region and therefore the z-score (where the standard deviation forms the denominator) is smaller. Thus this approach also addresses the third complication (iii) as discussed above.

Classification

An overall abnormality score Z is calculated on the entire lung fields by counting all locations x with z(x)>s and normalizing this to the number of locations in the lung field to account for the lung size. Z provides an appropriate decision criterion regarding the abnormality of a specific chest radiograph.

Summary

Below is provided a brief overview, including additional details relating to specific steps, of the model building, abnormality detection and rating, that have been described above in detail. The pre-processing outlined above can be an important pre-requisite step for this purpose. In some situations it is applied to all images included in the analysis (both to reference image(s) during a training phase to build the model, and to the unseen image during detection) in the same manner. Steps are further detailed here:

Lung field segmentation is achieved by a method described in the paper by D. Barthel and J. von Berg. Robust automatic lung field segmentation on digital chest radiographs. Int J CARS, 4(Suppl 1):326-327, 2009. Other known methods of segmentation can be used.

Bone suppression can also achieved by known methods, for example as described in the following sources: von Berg and Neitzel. Bone Suppression in X-ray radiograms. World patent WO 2011/077334; Jens von Berg, Stewart Young, Heike Carolus, Robin Wolz, Axel Saalbach, Alberto Hidalgo, Ana Gimenez, and Tomas Franquet, A novel bone suppression method that improves lung nodule detection, International Journal of Computer Assisted Radiology and Surgery, pp. 1-15, 2015; and von Berg, Levrier, Carolus, Young, Saalbach, Laurent, and, Florent. Decomposing the bony thorax in radiographs. In Proc of ISBI 2016 in print.

Intensity normalization can be achieved by determining an intensity quantile q of the lung fields, e.g. at 7.5% of the intensity range, the dark part of the lung fields. Normalization thus means to subtract q from the image (and add a constant in order not to get negative image intensities). This is a very simple method in contrast to others that are based on the analysis of complex texture and shape features.

Space normalization can be performed based upon the lung field contours made from a discrete set of step points. An average lung field model is built on a training set. This establishes the definition of the "atlas" (reference) space. All images can then be spatially aligned with this "atlas" space via a warping of the original image to co-align the lungs with those of the model. A B-spline method can be applied as described in the paper by Rueckert, Daniel, et al. Nonrigid registration using free-form deformations: application to breast MR images. Medical Imaging, IEEE Transactions on, 1999, 18[8], p. 712-721. Other approaches, such as k-nearest neighbour interpolation, could be applied.

Thus, an apparatus, system and method for the detection of opacities in X-ray images described here can be applied to automatically classify images having a high probability of being abnormal. This can serve as an automatic step to select interesting cases from a data base. It can be also used to identify patients having a certain risk of suffering from pulmonary diseases like Tuberculosis. In a screening scenario these patients could then be subject to further diagnostic testing with other means like a sputum test or a gene test. Also, visualizations like those in FIG. 7 can be presented to a person in charge of diagnosing pulmonary diseases like Tuberculosis, to support this person in becoming more confident with the diagnosis.

In another exemplary embodiment, a computer program or computer program element is provided that is characterized by being configured to execute the method steps of the method according to one of the preceding embodiments, an appropriate system.

The computer program element might therefore be stored on a computer unit, which might also be part of an embodiment. This computing unit may be configured to perform or induce performing of the steps of the method described above. Moreover, it may be configured to operate the components of the above described apparatus. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for detecting opacities in two-dimensional (2D) radiograph X-ray images, the system comprising:
    first processor circuitry configured to provide an analysis 2D radiograph X-ray image;
    an apparatus comprising:
        second processor circuitry configured to:
            receive the analysis 2D radiograph X-ray image of a region of interest of an analyzed body part;
            receive a model of a normal region of interest, wherein the model is based on a plurality of 2D radiograph X-ray images of the region of interest that is normal and does not suffer from abnormalities, wherein the model contains statistical information on a normal healthy population, and wherein the plurality of 2D radiograph X-ray images of the region of interest, on which the model of the normal region is based, have been intensity normalized;
            detect at least one abnormality in the region of interest of the analyzed body part, wherein the detection comprises: intensity normalizing the analysis 2D radiograph X-ray image, suppressing at least some bone related imagery in the analysis 2D radiograph X-ray image, and comparing the analysis 2D radiograph X-ray image and the model; and
            output information on the at least one abnormality; and
        a display configured to output the analysis 2D radiograph X-ray image comprising the information on the at least one abnormality.

2. A method for detecting opacities in clinical two-dimensional (2D) radiograph X-ray images, comprising:
    providing an analysis 2D radiograph X-ray image of a region of interest of an analyzed body part;
    providing a model of a normal region of interest, wherein the model is based on a plurality of 2D radiograph X-ray images of the region of interest that is normal and does not suffer from abnormalities, wherein the model contains statistical information on a normal healthy population, and wherein the plurality of 2D radiograph X-ray images of the region of interest, on which the model of the normal region is based, have been intensity normalized;

detecting at least one abnormality in the region of interest of the analyzed body part, wherein the detecting comprises:
intensity normalizing the analysis 2D radiograph X-ray image,
comparing the analysis 2D radiograph X-ray image and the model, and
suppressing at least some bone related imagery in the analysis 2D radiograph X-ray image; and outputting information on the at least one abnormality.

3. An apparatus for detecting opacities in clinical two-dimensional (2D) radiograph X-ray images, comprising:
processor circuitry configured to:
receive an analysis 2D radiograph X-ray image of a region of interest of an analyzed body part;
receive a model of a normal region of interest, wherein the model is based on a plurality of 2D radiograph X-ray images of the region of interest that is normal and does not suffer from abnormalities, wherein the model contains statistical information on a normal healthy population, and wherein the plurality of 2D radiograph X-ray images of the region of interest, upon which the model of the normal region is based, have been intensity normalized;
detect at least one abnormality in the region of interest of the analyzed body part, wherein the detection comprises:
intensity normalizing the analysis 2D radiograph X-ray image,
suppressing at least some bone related imagery in the analysis 2D radiograph X-ray image, and
comparing the analysis 2D radiograph X-ray image and the mode; and
output information on the at least one abnormality.

4. The apparatus according to claim 3, further comprising determining at least one deviation between at least one intensity in the region of interest of the analysis 2D radiograph X-ray image and a corresponding at least one intensity in the normal region of interest of the model.

5. The apparatus according to claim 3, wherein model data of the model comprises at least one average intensity based on corresponding intensities in the plurality of 2D radiograph X-ray images of the region of interest, the model data comprising at least one standard deviation intensity based on the corresponding intensities in the plurality of 2D radiograph X-ray images of the region of interest; and wherein the analysis 2D radiograph X-ray image and the model are compared based on at least one intensity value in the region of interest of the analysis 2D radiograph X-ray image, the at least one average intensity value in the normal region of interest of the model, and the at least one standard deviation intensity in the normal region of interest of the model.

6. The apparatus according to claim 5, wherein the analysis 2D radiograph X-ray image and the model are compared by determining a difference between an intensity at a spatial position in the analysis 2D radiograph X-ray image and an average intensity at a corresponding spatial position in the model, wherein the processor is further configured to determine a ratio between the difference and a standard deviation in intensity at the corresponding spatial position in the model.

7. The apparatus according to claim 3, further comprising determining at least one score based on at least one intensity in the region of interest of the analysis 2D radiograph X-ray image and a corresponding at least one intensity in the normal region of interest of the model.

8. The apparatus according to claim 7, wherein the at least one score is indicative that at least one abnormality is detected in the region of interest of the analyzed body part.

9. The apparatus according to claim 7, further comprising delineating at least one area of the region of interest of the analysis 2D radiograph X-ray image based on the at least one score.

10. The apparatus according to claim 3, wherein the plurality of 2D radiograph X-ray images of the region of interest upon which the model is based have had at least some bone related imagery suppressed.

11. The apparatus according to claim 3, wherein detecting the at least one abnormality in the region of interest of the analyzed body part comprises a registration of the region of interest of the analysis 2D radiograph X-ray image to the normal region of interest of the model.

12. The apparatus according to claim 3, wherein the comparing of the analysis 2D radiograph X-ray image and the model includes comparing:
the analysis 2D radiograph X-ray image that had the at least some bone related imagery suppressed, and
the model, wherein the plurality of 2D radiograph X-ray images of the region of interest upon which the model is based had at least some bone related imagery suppressed.

13. A non-transitory computer-readable medium having one or more executable instructions stored thereon, which, when executed by processor circuitry, cause the processor circuitry to perform a method for detecting opacities in clinical two-dimensional (2D) radiograph X-ray images, the method comprising:
providing an analysis 2D radiograph X-ray image of a region of interest of an analyzed body part;
providing a model of a normal region of interest, wherein the model is based on a plurality of 2D radiograph X-ray images of the region of interest that is normal and does not suffer from abnormalities, wherein the model contains statistical information on a normal healthy population, and wherein the plurality of 2D radiograph X-ray images of the region of interest, upon which the model of the normal region is based, have been intensity normalized;
detecting at least one abnormality in the region of interest of the analyzed body part, wherein the detection comprises:
intensity normalizing the analysis 2D radiograph X-ray image,
comparing the analysis 2D radiograph X-ray image and the model, and
suppressing at least some bone related imagery in the analysis 2D radiograph X-ray image; and
outputting information on the at least one abnormality.

* * * * *